(12) United States Patent
Headley

(10) Patent No.: US 9,439,794 B2
(45) Date of Patent: Sep. 13, 2016

(54) MEDICAL DEVICE DELIVERY CATHETER AND MEDICAL DEVICE DELIVERY SYSTEM USING SAME

(71) Applicant: Cook Medical Technologies LLC, Bloomington, IN (US)

(72) Inventor: Joshua P. Headley, Ellettsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 227 days.

(21) Appl. No.: 13/917,704

(22) Filed: Jun. 14, 2013

(65) Prior Publication Data

US 2014/0025152 A1    Jan. 23, 2014

Related U.S. Application Data

(60) Provisional application No. 61/672,506, filed on Jul. 17, 2012.

(51) Int. Cl.
*A61F 2/962*    (2013.01)

(52) U.S. Cl.
CPC ..................... *A61F 2/962* (2013.01)

(58) Field of Classification Search
CPC ............ A61F 2/95; A61F 2002/9505; A61F 2002/9511; A61F 2/958; A61F 2002/9583; A61F 2002/9665; A61F 2002/011; A61F 2/2427; A61F 2/243; A61F 2/2433; A61F 2/2436; A61F 2/2442; A61F 2/962; A61M 25/00; A61M 25/0021; A61M 25/0054; A61M 2025/0042; A61M 25/008; A61M 25/0068; A61M 25/01; A61M 25/0105; A61M 25/09; A61M 25/0052; A61M 25/0051; A61M 25/005; A61M 25/0053; A61M 25/0081
USPC ............................................... 623/1.11–1.15
See application file for complete search history.

(56) References Cited

U.S. PATENT DOCUMENTS

| | | | |
|---|---|---|---|
| 6,475,209 B1 | 11/2002 | Larson et al. | |
| 7,566,342 B2 | 7/2009 | Parker et al. | |
| 7,981,148 B2 | 7/2011 | Aguilar et al. | |
| 8,449,526 B2* | 5/2013 | Snyder | A61M 25/0051 604/525 |
| 2006/0100687 A1* | 5/2006 | Fahey et al. | 623/1.11 |
| 2007/0208405 A1 | 9/2007 | Goodin et al. | |
| 2010/0125280 A1 | 5/2010 | Molloy | |

* cited by examiner

*Primary Examiner* — Wade Miles
*Assistant Examiner* — George J Ulsh
(74) *Attorney, Agent, or Firm* — Liell & McNeil

(57) ABSTRACT

A medical device delivery catheter includes an elongate tubular body including proximal, intermediate, and distal longitudinal segments. The proximal segment extends between a proximal end of the body and a first transition between the proximal segment and the intermediate segment, has a first outer diameter, and includes at least one flexibility increasing cut through a wall of the body. The intermediate segment extends between the first transition and a second transition between the intermediate segment and the distal segment, has a second outer diameter that is less than the first outer diameter, and defines a medical device support region. The distal segment has an initial outer diameter that is greater than the second outer diameter and terminates in a distally tapered region. The body is free of joints and has a uniform tensile strength across the proximal, intermediate, and distal segments and the transitions.

20 Claims, 2 Drawing Sheets

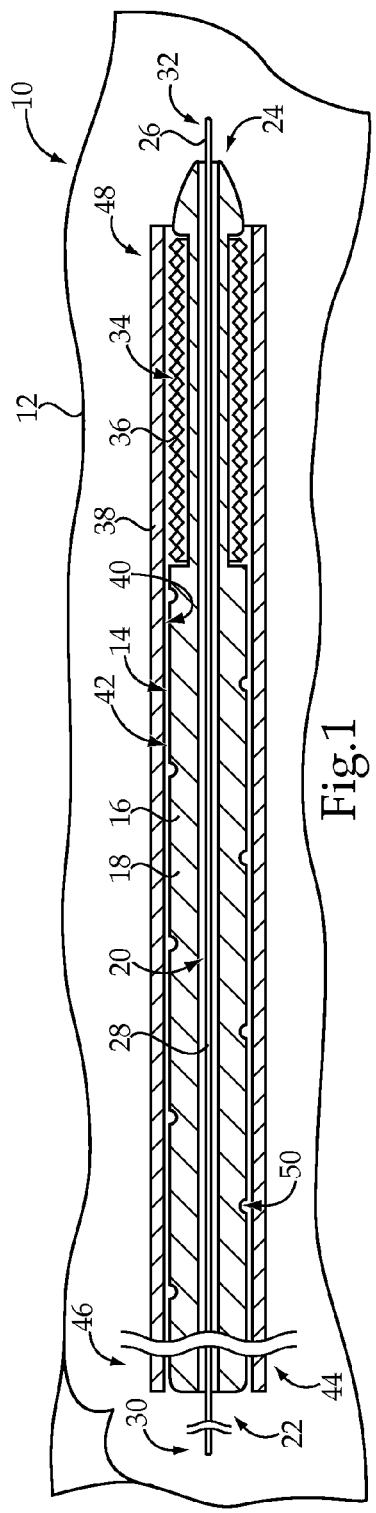
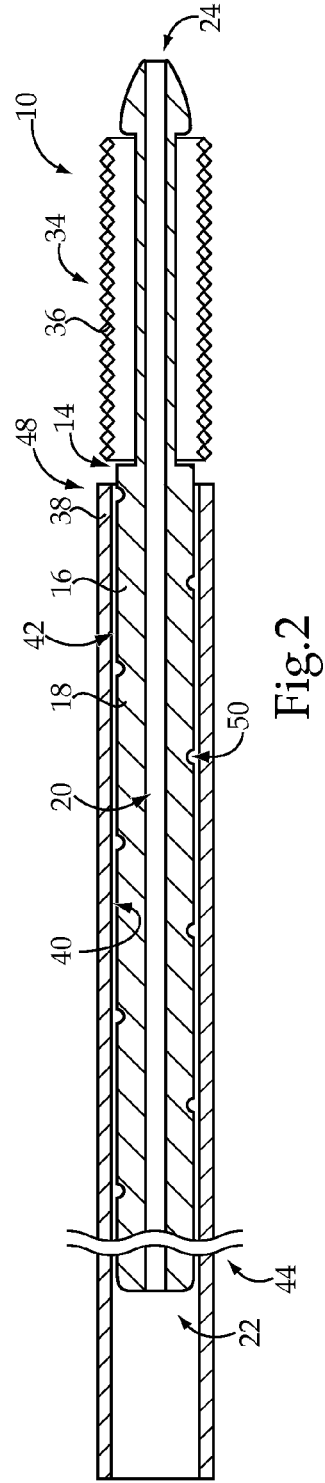
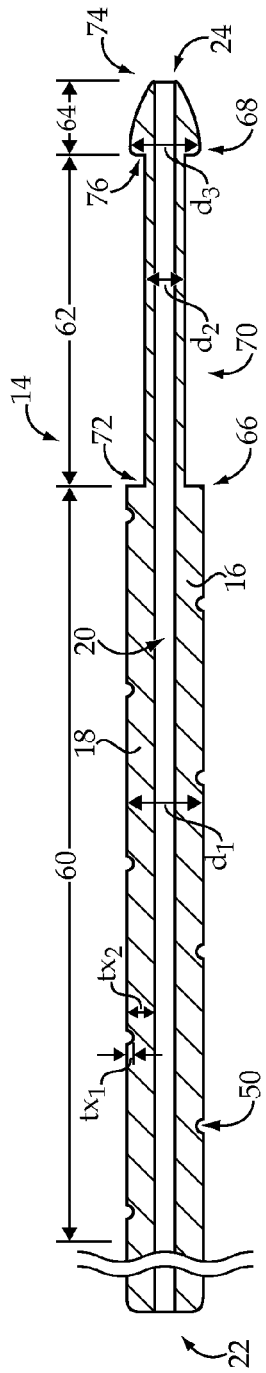

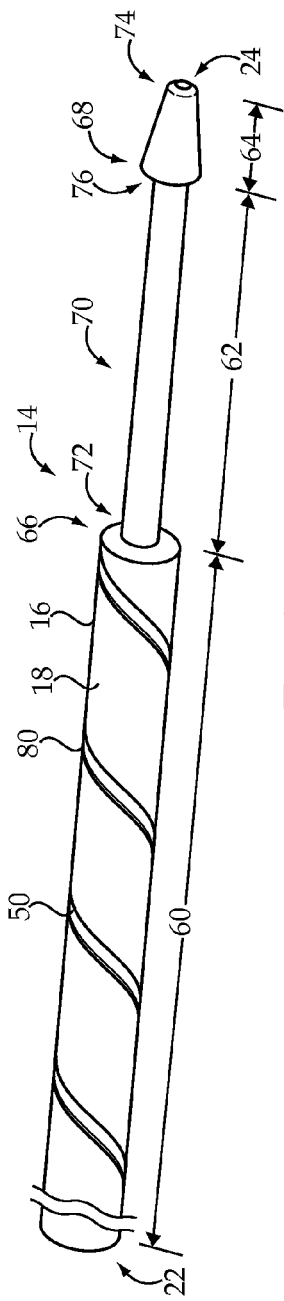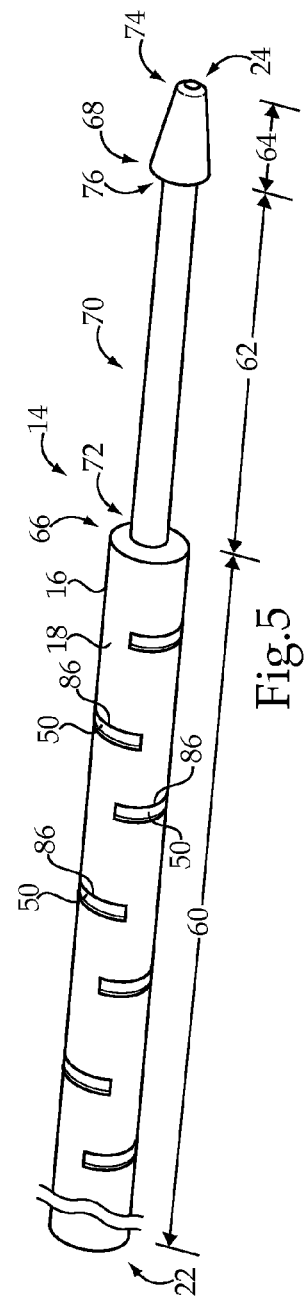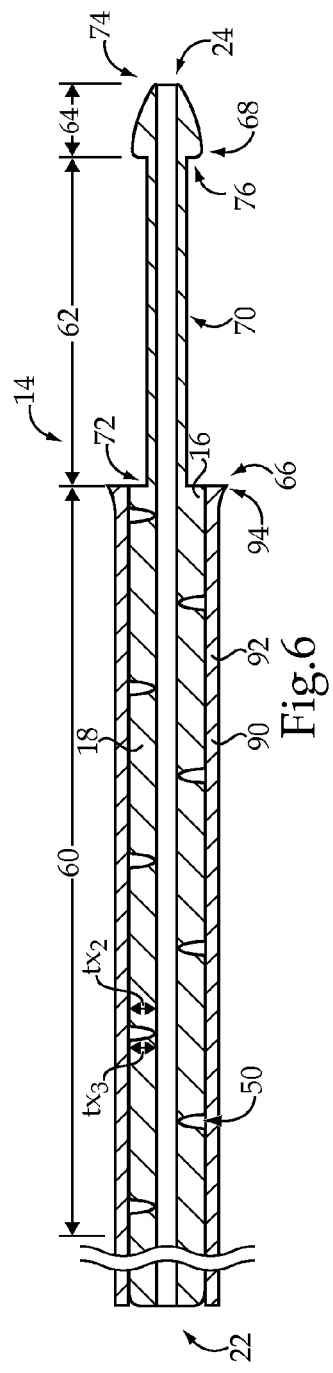

MEDICAL DEVICE DELIVERY CATHETER AND MEDICAL DEVICE DELIVERY SYSTEM USING SAME

RELATION TO OTHER PATENT APPLICATION

This application claims priority to provisional patent application 61/672,506, filed on Jul. 17, 2012, with the same title.

TECHNICAL FIELD

The present disclosure relates generally to a medical device delivery catheter for use with a medical device delivery system, and more particularly to a medical device delivery catheter free of joints.

BACKGROUND

Interventional devices, such as stents, are often introduced percutaneously into the body of a patient using a medical device delivery system. The medical device delivery system typically includes a medical device delivery catheter configured to support the stent, or other medical device, as the stent is delivered to a target site within the body. The stent may then be deployed at the target site within the lumen of a vessel or other bodily passageway to reinforce, repair, or otherwise provide support for the body lumen. For example, when a patient suffers from atherosclerosis, a stent may be placed in a coronary or a peripheral artery at a location where the artery is weakened or damaged. The stent, once in place, may reinforce that portion of the artery, thereby restoring normal blood flow through the vessel.

The medical device delivery catheter may obtain the necessary axial strength by relying on lengths of tubing having different axial strengths. For example, the more proximal segments of the inner catheter member may utilize tubing that has increased axial strength to allow a clinician to push the catheter portion of the delivery system through the lumen. The more distal segments of the delivery catheter may be made from a more flexible tubing to provide needed flexibility at the distal end, which often navigates tortuous and narrow body passageways. As a result, the delivery catheter is often made from a number of different tubular segments bonded together to create a composite structure. From a manufacturing standpoint, the bonding of different tubular segments together may increase the overall cost of the medical device delivery catheter and thus, the delivery system, since the bonding process can often be labor intensive. Additionally, there is a possibility that the delivery catheter could be separated at one of the joints as the clinician is retracting the delivery catheter from the patient.

The present disclosure is directed toward one or more of the problems set forth above.

SUMMARY OF THE DISCLOSURE

In one aspect, a medical device delivery catheter includes an elongate tubular body including a proximal longitudinal segment, an intermediate longitudinal segment, and a distal longitudinal segment. The proximal longitudinal segment extends between a proximal end of the elongate tubular body and a first transition between the proximal longitudinal segment and the intermediate longitudinal segment, has a first outer diameter, and includes at least one flexibility increasing cut through a wall of the elongate tubular body. The intermediate longitudinal segment extends between the first transition and a second transition between the intermediate longitudinal segment and the distal longitudinal segment, has a second outer diameter that is less than the first outer diameter, and defines a medical device support region. The distal longitudinal segment has an initial outer diameter that is greater than the second outer diameter and terminates in a distally tapered region. The elongate tubular body is free of joints and has a uniform tensile strength across the proximal, intermediate, and distal longitudinal segments and the first and second transitions.

In another aspect, a medical device delivery system includes a medical device delivery catheter having an elongate tubular body including a proximal longitudinal segment, an intermediate longitudinal segment, and a distal longitudinal segment. The proximal longitudinal segment extends between a proximal end of the elongate tubular body and a first transition between the proximal longitudinal segment and the intermediate longitudinal segment, has a first outer diameter, and includes at least one flexibility increasing cut through a wall of the elongate tubular body. The intermediate longitudinal segment extends between the first transition and a second transition between the intermediate longitudinal segment and the distal longitudinal segment, has a second outer diameter that is less than the first outer diameter, and defines a medical device support region. The distal longitudinal segment has an initial outer diameter that is greater than the second outer diameter and terminates in a distally tapered region. The elongate tubular body is free of joints and has a uniform tensile strength across the proximal, intermediate, and distal longitudinal segments and the first and second transitions. The medical device delivery system also includes a medical device positioned over the elongate tubular body at the medical device support region, and an elongate tubular sheath slidably received over the elongate tubular body. One of the elongate tubular sheath and the elongate tubular body is movable relative to another of the elongate tubular sheath and the elongate tubular body between a delivery configuration in which the elongate tubular sheath restricts radial expansion of the medical device and a deployment configuration in which the medical device is not restricted from radial expansion by the elongate tubular sheath.

BRIEF DESCRIPTION OF THE DRAWINGS

FIG. 1 is a longitudinal sectional view of a medical device delivery system, shown in a delivery configuration, according to one embodiment of the present disclosure;

FIG. 2 is a longitudinal sectional view of the medical device delivery system of FIG. 1, shown in a deployment configuration;

FIG. 3 is a longitudinal sectional view of the medical device delivery catheter of the medical device delivery system shown in FIGS. 1 and 2;

FIG. 4 is a perspective view of a distal segment of a medical device delivery catheter of the present disclosure, illustrating one embodiment of a flexibility increasing cut through a wall of the elongate tubular body;

FIG. 5 is a perspective view of a distal segment of a medical device delivery catheter of the present disclosure, illustrating another embodiment of a flexibility increasing cut through the elongate tubular body; and FIG. 6 is a longitudinal sectional view of another embodiment of a medical device delivery catheter, including a support material layer.

DETAILED DESCRIPTION

Referring to FIG. 1, there is shown a medical device delivery system 10, according to one embodiment of the present disclosure. The medical device delivery system 10 may include a number of components, which may be provided within a sterile, tear open package 12, as is known in the art. In performing a medical device delivery procedure, some or all of the components of the medical device delivery system 10 may be used, depending upon the specifics of the procedure to be performed. As should be appreciated, however, the components shown in FIG. 1 might be separately packaged and/or the medical device delivery system 10 might also include components in addition to those shown, including components routinely used in percutaneous vascular procedures.

The medical device delivery system 10 includes a medical device delivery catheter 14 having an elongate tubular body 16. The elongate tubular body 16 generally includes a catheter wall 18 defining a lumen 20 extending from an open proximal end 22 to an open distal end 24 of the elongate tubular body 16. As used herein, "proximal" will be used to refer to the end of a component or feature that is closest to a clinician, while "distal" is used to refer to a component or feature that is farthest away from the clinician. The elongate tubular body 16 may range in length from several inches to several feet long, and may have a catheter wall diameter that is orders of magnitude smaller than its length. Although a single lumen 20 is shown, it should be appreciated that the medical device delivery catheter 14 may include two or more lumens extending through most or all of the length of the elongate tubular body 16, or may be a solid shaft that does not include a lumen.

According to the exemplary embodiment, the medical device delivery system 10 may include a wire guide 26 received within the lumen 20. A wire guide, such as wire guide 26, is a device commonly used in percutaneous vascular procedures to introduce a wide variety of medical devices into the vascular system. Generally speaking, the wire guide 26 includes an elongate flexible body 28 extending from a proximal end 30 to a distal end 32. Since wire guides are known, wire guide 26 will not be discussed herein in greater detail. However, it should be noted that wire guide 26 may be made from any of a number of known materials commonly used to manufacture medical devices and may include any of a variety of known configurations. For example, some wire guides include an elongate core element with one or more tapered sections near a distal end thereof. According to all embodiments, the dimensions and materials of the wire guide 26 may be selected to enhance advancement through the vasculature of the patient, while maintaining an outer diameter that facilitates advancement of the other components of the medical device delivery system 10 over the wire guide 26.

As shown, the medical device delivery catheter 14 is configured to support a medical device 34 thereon. According to the exemplary embodiment, the medical device 34 may include a radially expanding stent 36 for providing tubular support within a blood vessel, canal, duct, or other bodily passageway. Radially expandable stents 36 are known and may be expanded using a balloon positioned at a distal portion of a delivery catheter. Alternatively, and according to the exemplary embodiment, the stent 36 may be made from a resilient or shape memory material, such as, for example, nitinol, that is capable of self-expanding from a compressed state to an expanded state without the application of a radial force on the stent 36. Such a stent 36 may be referred to as a "self-expanding" stent 36.

The self-expanding stent 36 may be loaded onto the medical device delivery catheter 14, as shown, and may be restricted from self-expansion using an elongate tubular sheath 38 slidably received over the elongate tubular body 16 of the medical device delivery catheter 14. According to this delivery configuration, the elongate tubular sheath 38 restricts radial expansion of the self-expanding stent 36 by contacting the stent 36 with an inner wall surface 40 defining a lumen 42 of the elongate tubular sheath 38. Once the medical device delivery system 10 is directed to the target site, the system 10 may be moved from the delivery configuration into a deployment configuration. According to the deployment configuration, as shown in FIG. 2, the stent 36 is no longer restricted from radial expansion by the elongate tubular sheath 38. In particular, the elongate tubular sheath 38 may be withdrawn such that it no longer covers the self-expanding stent 36. For example, a proximal end 44 of the elongate tubular sheath 38 may be grasped and pulled to proximally withdraw the elongate tubular sheath 38. As a result, the radially expanding stent 36 self-expands to the desired diameter.

Although not shown, a handle or retraction mechanism may be provided at a proximal end 46 of the medical device delivery system 10 to aid in the deployment of the self-expanding stent 36. In particular, a handle may be provided to facilitate movement of the medical device delivery system 10 between the delivery and deployment configurations, as shown in FIGS. 1 and 2, respectively. It should be appreciated that the medical device delivery system 10 may include a variety of additional and/or alternative components useful in carrying out a medical device delivery procedure. It should further be appreciated that although the medical device delivery system 10 is described in the context of a stent delivery system, the medical device delivery catheter 14 described herein may have broader applicability beyond stent delivery procedures.

The medical device delivery catheter 14 and elongate tubular sheath 38 may be made from any common medical tube materials or polymers, such as, for example, PTFE, HDPE, nylon, PEEK, polyamide, polyimide, or any vinyl, plastic, rubber, or silicone, and may exhibit both stiffness, or firmness, and flexibility. Materials as well as dimensions may vary depending on specific requirements of the medical device delivery procedure being performed. However, according to all embodiments, the medical device delivery catheter 14 and elongate tubular sheath 38 are sized such that the medical device delivery catheter 14 may be telescopically received within, and movable through, the elongate tubular sheath 38.

According to the delivery configuration of FIG. 1, in which the medical device delivery system 10 is advanced to a target site, the medical device delivery catheter 14 may extend distally beyond a distal end 48 of the elongate tubular sheath 38. As such, the elongate tubular body 16 may distally taper to define an atraumatic tip, as shown. According to some embodiments, the distal end 48 of the elongate tubular sheath 38 may also include a distal taper. The medical device delivery catheter 14 may also include one or more flexibility increasing cuts 50 through the catheter wall 18, as will be discussed in greater detail below.

According to the present disclosure, the medical device delivery catheter 14 or, more specifically, the elongate tubular body 16 is free of joints. In particular, the elongate tubular body 16 is a single, or one-piece, component having a proximal longitudinal segment 60, an intermediate longitudinal segment 62, and a distal longitudinal segment 64, as is shown in FIG. 3. The proximal longitudinal segment 60 extends between the proximal end 22 of the elongate tubular body 16 and a first transition 66 between the proximal longitudinal segment 60 and the intermediate longitudinal segment 62. The proximal longitudinal segment 60 has a first outer diameter $d_1$ and may include the flexibility increasing cut 50 introduced above. According to some embodiments, the proximal longitudinal segment 60 may extend a majority of a length of the elongate tubular body 16.

The intermediate longitudinal segment 62 extends between the first transition 66 and a second transition 68 between the intermediate longitudinal segment 62 and the distal longitudinal segment 64. The intermediate longitudinal segment 62 has a second outer diameter $d_2$ that is less than the first outer diameter $d_1$ and defines a medical device support region 70, which may be configured to the support the radially expanding stent 36 described above. The first transition 66, which may include an abrupt decrease in outer diameter from the first outer diameter $d_1$ to the second outer diameter $d_2$, may define a shoulder 72 that reduces proximal movement or refraction of the radially expanding stent 36 during movement of the medical device delivery system 10 from the delivery configuration of FIG. 1 to the deployment configuration of FIG. 2. In particular, the shoulder 72 may reduce axial movement in the proximal direction of the stent 36 as one of the medical device delivery catheter 14 and the elongate tubular sheath 38 is moved relative to the other. The intermediate longitudinal segment 62 may have an outer diameter $d_2$ and axial length sufficient to support a medical device 34, such as stent 36, thereon, particularly in the delivery configuration.

The distal longitudinal segment 64 extends distally from the second transition 68 and, according to the exemplary embodiment, terminates at an atraumatic tip 74. The distal longitudinal segment 64 has an initial outer diameter $d_3$ that is greater than the second outer diameter $d_2$ and terminates in a distally tapered region. The second transition 68 may include an abrupt increase in outer diameter from the second outer diameter $d_2$ to the initial outer diameter $d_3$ of the distal longitudinal segment 64. As such, the first and second transitions 66 and 68 may both function to define the medical device support region 70 and reduce axial movement, in both the proximal and distal directions, of the radially expanding stent 36 during movement of the medical device delivery system 10. More specifically, the second transition 68 may also define a shoulder, shown at 76.

Typically, a medical device delivery catheter, such as medical device delivery catheter 14, will be made from a number of different tubular segments bonded together to create a composite structure including the different longitudinal segments described above. As such, a typical medical device delivery catheter will include a number of joints interconnecting the different longitudinal segments. As stated above, the elongate tubular body 16 of the medical device delivery catheter 14 of the present disclosure is free of joints and, thus, has a uniform tensile strength per unit area across the proximal, intermediate, and distal longitudinal segments 60, 62, and 64 and the first and second transitions 66 and 68. To make such a single or one-piece medical device delivery catheter 14, any of a variety of different machining methods may be employed.

According to an exemplary manufacturing method, the distal end 24 of the elongate tubular body 16 may profiled to shape the atraumatic tip 74. Such profiling may be achieved using grinding, such as centerless grinding, or other known manufacturing methods, which may include shaping, molding, and material removal. A similar grinding method may be used to remove material from the elongate tubular body 16 to define the second outer diameter $d_2$ of the medical device support region 70. As stated above, the second transition 68 between the intermediate longitudinal region 62 and the distal longitudinal region 64 may include an abrupt transition between the initial outer diameter $d_3$ of the profiled atraumatic tip 74 and the decreased outer diameter $d_2$ of the medical device support region 70. According to alternative embodiments, a gradual transition may be desired.

The grinding, or other similar manufacturing process, may be adjusted at the first transition 66 to increase the second outer diameter $d_2$ of the intermediate longitudinal segment 62 to the first outer diameter $d_1$ of the proximal longitudinal segment 60. As stated above, the first transition 66, similar to the second transition 68, may be an abrupt transition to define the appropriate axial support for the medical device 34 to be supported along the medical device support region 70. As should be appreciated, the single tubing, such as a polymeric tubing, may be provided with the lumen 20 and later shaped using known manufacturing processes to form the elongate tubular body 16 having the characteristics of the proximal, intermediate, and distal longitudinal segments 60, 62, and 64.

The medical device delivery catheter 14, or at least a majority of the length of the medical device delivery catheter 14, should be sufficiently flexible to pass through a tight curvature or tortuous passageway. The ability of a catheter to bend and advance effectively through vascular structures or other lumens is commonly referred to as the "trackability" of the catheter. However, the catheter should also be "pushable," meaning that longitudinal forces are transmitted along the catheter from the proximal end to the distal end such that a physician can push the catheter through the vascular structures. The medical device delivery catheter 14, along with the elongate tubular sheath 38, should be both trackable and pushable. In other words, the elongate tubular body 16 should be flexible yet stiff.

The decreased outer diameter $d_2$ of the intermediate longitudinal segment 62 and the profiled atraumatic tip 74 of the distal longitudinal segment 64 may have sizes and shapes that provide the requisite flexibility and stiffness, particularly when advanced through a vascular structure in conjunction with the elongate tubular sheath 38, as described above. However, to provide the increased outer diameter $d_1$ of the proximal longitudinal segment 60, the catheter wall 18 of the elongate tubular body 16 at the proximal longitudinal segment 60 may be relatively thick. As such, the one or more flexibility increasing cuts 50 may be provided through the wall 18 of the elongate tubular body 16. The flexibility increasing cut or cuts 50 may be provided only partially through the catheter wall 18 (i.e., may have a depth $tx_1$ less than the wall thickness $tx_2$), and may have any width, or shape.

As shown in FIG. 4, the at least one flexibility increasing cut 50 may include a single continuous spiral cut 80 through the catheter wall 18. Alternatively, as shown in FIG. 5, a plurality of discontinuous cuts 86 may be provided. As previously stated, any number, shape, size, and pattern of cuts 50 may be provided through the wall 18 of the elongate tubular body 16, particularly at the proximal longitudinal segment 60. The cuts 50 may be provided along the entire length of the proximal longitudinal segment 60 or may be provided along specific portions. It should be appreciated that such determinations may be made based on the desired flexibility required for the particular procedure or based on the ease of manufacturing.

Turning now to FIG. 6, it may be desirable to form the cuts 50 all the way through the catheter wall 18. In particular, the thickness $tx_3$ of the cuts of FIG. 6 may be equal to the wall thickness $tx_2$. According to such embodiments, it may also be desirable to provide a support material layer 90 over all or portions of the proximal longitudinal segment 60. For example, the support material layer 90 may include a nylon material 92 and may be applied to the elongate tubular housing 16 using a heat shrink method, or other method known in the art. According to some embodiments, and as shown in FIG. 6, the support material layer 90 may include a distally expanding outer diameter, or flare 96, to further support the axial position of the medical device 34 supported along the intermediate longitudinal segment 62. Although not shown, some embodiments may incorporate radiopaque bands or markers to facilitate or improve device positioning.

INDUSTRIAL APPLICABILITY

The present disclosure is generally applicable to medical device delivery systems, such as stent delivery systems. More specifically, the present disclosure finds application with medical device delivery catheters for use in such medical device delivery systems. Yet further, the present disclosure finds potential application in medical device delivery catheters that are free joints and, thus, have a uniform tensile strength per unit area along the length of the catheter.

Referring generally to FIGS. 1-6, a medical device delivery system 10 includes a medical device delivery catheter 14 having an elongate tubular body 16. The elongate tubular body 16 generally includes a catheter wall 18 defining a lumen 20 extending from an open proximal end 22 to an open distal end 24 of the elongate tubular body 16. The medical device delivery system 10 may include a wire guide 26 received within the lumen 20. The medical device delivery catheter 14 is configured to support a medial device 34, such as a stent 36, thereon. The self-expanding stent 36 may be loaded onto the medical device delivery catheter 14, as shown, and may be restricted from self-expansion using an elongate tubular sheath 38 slidably received over the elongate tubular body 16 of the medical device delivery catheter 14. According to this delivery configuration, the elongate tubular sheath 38 restricts radial expansion of the self-expanding stent 36 by contacting the stent 36 with an inner wall surface 40 defining a lumen 42 of the elongate tubular sheath 38. Once the medical device delivery system 10 is directed to the target site, the system 10 may be moved from the delivery configuration into a deployment configuration. According to the deployment configuration, as shown in FIG. 2, the stent 36 is no longer restricted from radial expansion by the elongate tubular sheath 38. As a result, the radially expanding stent 36 self-expands to the desired diameter.

According to the present disclosure, the medical device delivery catheter 14 or, more specifically, the elongate tubular body 16 is free of joints. In particular, the elongate tubular body 16 is a single, or one-piece, component having a proximal longitudinal segment 60, an intermediate longitudinal segment 62, and a distal longitudinal segment 64, as is shown in FIG. 3. The proximal longitudinal segment 60 extends between the proximal end 22 of the elongate tubular body 16 and a first transition 66 between the proximal longitudinal segment 60 and the intermediate longitudinal segment 62. The proximal longitudinal segment 60 has a first outer diameter $d_1$ and a may include at least one flexibility increasing cut 50. According to some embodiments, the proximal longitudinal segment 60 may extend a majority of a length of the elongate tubular body 16.

The intermediate longitudinal segment 62 extends between the first transition 66 and a second transition 68 between the intermediate longitudinal segment 62 and the distal longitudinal segment 64. The intermediate longitudinal segment 62 has a second outer diameter $d_2$ that is less than the first outer diameter $d_1$ and defines a medical device support region 70, which may be configured to the support the radially expanding stent 36 described above. The first transition 66, which may include an abrupt decrease in outer diameter from the first outer diameter $d_1$ to the second outer diameter $d_2$, may define a shoulder 72 that reduces proximal movement or refraction of the radially expanding stent 36 during movement of the medical device delivery system 10 from the delivery configuration of FIG. 1 to the deployment configuration of FIG. 2. In particular, the shoulder 72 may reduce axial movement in the proximal direction of the stent 36 as one of the medical device delivery catheter 14 and the elongate tubular sheath 38 is moved relative to the other.

The distal longitudinal segment 64 extends distally from the second transition 68 and, according to the exemplary embodiment, terminates at an atraumatic tip 74. The distal longitudinal segment 64 has an initial outer diameter $d_3$ that is greater than the second outer diameter $d_2$ and terminates in a distally tapered region. The second transition 68 may include an abrupt increase in outer diameter from the second outer diameter $d_2$ to the initial outer diameter $d_3$ of the distal longitudinal segment 64. As such, the first and second transitions 66 and 68 may function to define the medical device support region 70 and reduce axial movement, in both the proximal and distal directions, of the radially expanding stent 36 during movement of the medical device delivery system 10.

Typically, a medical device delivery catheter will be made from a number of different tubular sections bonded together to create a composite unit including the proximal, intermediate, and distal longitudinal segments described above. As such, a typical medical device delivery catheter will include a number of joints interconnecting the different longitudinal segments. As stated above, the elongate tubular body of the medical device delivery catheter of the present disclosure is free of joints and, thus, has a uniform tensile strength per unit area across the proximal intermediate, and distal longitudinal segments and the first and second transitions. To make such a single or one-piece medical device delivery catheter, any of a variety of different machining methods, including those described herein, may be employed.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:
1. A medical device delivery catheter, comprising:
a one-piece elongate tubular body including a proximal longitudinal segment, an intermediate longitudinal segment, and a distal longitudinal segment;
wherein the proximal longitudinal segment extends between a proximal end of the elongate tubular body and a first transition between the proximal longitudinal segment and the intermediate longitudinal segment, has a first outer diameter, and includes at least one flexibility increasing cut through a wall of the elongate tubular body;
wherein the intermediate longitudinal segment extends between the first transition and a second transition between the intermediate longitudinal segment and the distal longitudinal segment, has a second outer diam- eter that is less than the first outer diameter, and defines a medical device support region;

wherein the distal longitudinal segment has an initial outer diameter that is greater than the second outer diameter and terminates in a distally tapered region;

wherein the elongate tubular body is free of joints and has a uniform tensile strength per unit area across the proximal, intermediate, and distal longitudinal segments and the first and second transitions.

2. The medical device delivery catheter of claim 1, wherein the at least one flexibility increasing cut includes a plurality of discontinuous cuts.

3. The medical device delivery catheter of claim 1, wherein the at least one flexibility increasing cut includes a single continuous spiral cut.

4. The medical device delivery catheter of claim 1, further including a support material layer extending over the proximal longitudinal segment.

5. The medical device delivery catheter of claim 4, wherein the support material layer includes a nylon material.

6. The medical device delivery catheter of claim 4, wherein the support material layer has a distally expanding outer diameter.

7. The medical device delivery catheter of claim 1, wherein the proximal longitudinal segment extends a majority of a length of the elongate tubular body.

8. The medical device delivery catheter of claim 1, wherein the elongate tubular body includes a polymer.

9. A medical device delivery system, comprising:
a medical device delivery catheter having a one-piece elongate tubular body including a proximal longitudinal segment, an intermediate longitudinal segment, and a distal longitudinal segment, wherein the proximal longitudinal segment extends between a proximal end of the elongate tubular body and a first transition between the proximal longitudinal segment and the intermediate longitudinal segment, has a first outer diameter, and includes at least one flexibility increasing cut through a wall of the elongate tubular body, wherein the intermediate longitudinal segment extends between the first transition and a second transition between the intermediate longitudinal segment and the distal longitudinal segment, has a second outer diameter that is less than the first outer diameter, and defines a medical device support region, wherein the distal longitudinal segment has an initial outer diameter that is greater than the second outer diameter and terminates in a distally tapered region, wherein the elongate tubular body is free of joints and has a uniform tensile strength per unit area across the proximal, intermediate, and distal longitudinal segments and the first and second transitions;
a medical device positioned over the elongate tubular body at the medical device support region; and
an elongate tubular sheath slidably received over the elongate tubular body;
wherein one of the elongate tubular sheath and the elongate tubular body is movable relative to another of the elongate tubular sheath and the elongate tubular body between a delivery configuration in which the elongate tubular sheath restricts radial expansion of the medical device and a deployment configuration in which the medical device is not restricted from radial expansion by the elongate tubular sheath.

10. The medical device delivery system of claim 9, wherein the at least one flexibility increasing cut includes a plurality of discontinuous cuts.

11. The medical device delivery system of claim 9, wherein the at least one flexibility increasing cut includes a single continuous spiral cut.

12. The medical device delivery system of claim 9, further including a support material layer extending over the proximal longitudinal segment.

13. The medical device delivery system of claim 12, wherein the support material layer includes a nylon material.

14. The medical device delivery system of claim 12, wherein the support material layer has a distally expanding outer diameter.

15. The medical device delivery system of claim 9, wherein the proximal longitudinal segment extends a majority of a length of the elongate tubular body.

16. The medical device delivery system of claim 9, wherein the elongate tubular body includes a polymer.

17. The medical device delivery system of claim 9, wherein the medical device is a stent.

18. The medical device delivery system of claim 17, wherein the stent is self-expandable in a radial direction.

19. The medical device delivery system of claim 1 wherein the flexibility increasing cut has a depth that is less than a thickness of the wall.

20. A medical device delivery catheter, comprising: a one-piece elongate tubular body including a proximal longitudinal segment, an intermediate longitudinal segment, and a distal longitudinal segment; wherein the proximal longitudinal segment extends between a proximal end of the elongate tubular body and a first transition between the proximal longitudinal segment and the intermediate longitudinal segment, has a first outer diameter, and includes at least one flexibility increasing cut through a wall of the elongate tubular body; wherein the intermediate longitudinal segment extends between the first transition and a second transition between the intermediate longitudinal segment and the distal longitudinal segment, has a second outer diameter that is less than the first outer diameter, and defines a medical device support region; and wherein the distal longitudinal segment has an initial outer diameter that is greater than the second outer diameter and terminates in a distally tapered region, wherein the elongate tubular body is free of joints and has a uniform tensile strength per unit area across the proximal, intermediate, and distal longitudinal segments and the first and second transitions.

* * * * *